United States Patent [19]
Wessendorf

[11] Patent Number: 5,416,448
[45] Date of Patent: May 16, 1995

[54] OSCILLATOR CIRCUIT FOR USE WITH HIGH LOSS QUARTZ RESONATOR SENSORS

[75] Inventor: Otto Wessendorf, Albuquerque, N. Mex.

[73] Assignee: Sandia Corporation, Albuquerque, N. Mex.

[21] Appl. No.: 108,935

[22] Filed: Aug. 18, 1993

[51] Int. Cl.$^6$ .................. H03B 5/30; G01R 27/26
[52] U.S. Cl. .................. 331/116 R; 331/109; 331/183; 331/65; 331/158; 73/290 V; 73/290 R; 310/316
[58] Field of Search .................. 331/65, 109, 116 R, 331/158, 183, 160, 163, 116 FE, 116 M; 324/727, 653; 310/316, 317, 321, 338; 73/290 V, 290 R

[56] References Cited

U.S. PATENT DOCUMENTS

| | | | |
|---|---|---|---|
| 3,649,929 | 3/1972 | Thompson | 331/61 |
| 3,986,145 | 10/1976 | Hongu et al. | 332/16 T |
| 4,001,718 | 1/1977 | Wilson et al. | 331/65 |
| 4,358,742 | 11/1982 | Ferriss | 331/158 |
| 4,588,968 | 5/1986 | Wile | 331/109 |
| 4,661,785 | 4/1987 | Benjaminson | 331/109 |
| 4,817,430 | 4/1989 | Benes et al. | 73/579 |
| 4,912,976 | 4/1990 | Labriola | 73/290 R |
| 4,914,406 | 4/1990 | Ohkubo | 331/116 R |
| 5,025,231 | 6/1991 | Schwartzbach | 331/116 R |
| 5,113,153 | 5/1992 | Soyuer | 331/61 R |

Primary Examiner—Robert J. Pascal
Assistant Examiner—Arnold Kinkead
Attorney, Agent, or Firm—Dennis F. Armijo

[57] ABSTRACT

The disclosure is directed to a Lever oscillator for use in high resistance resonator applications, especially for use with quartz resonator sensors. The oscillator is designed to operate over a wide dynamic range of resonator resistance due to damping of the resonator in mediums such as liquids. An oscillator design is presented that allows both frequency and loss ($R_m$) of the resonator to be determined over a wide dynamic range of resonator loss. The Lever oscillator uses negative feedback in a differential amplifier configuration to actively and variably divide (or leverage) the resonator impedance such that the oscillator can maintain the phase and gain of the loop over a wide range of resonator resistance.

15 Claims, 10 Drawing Sheets

OSCILLATOR CIRCUIT FOR USE WITH HIGH LOSS QUARTZ RESONATOR SENSORS

GOVERNMENT RIGHTS

The U.S. Government has a paid-up license to this invention and the right in limited circumstances to require the patent owner to license others on reasonable terms.

BACKGROUND OF THE INVENTION

1. Field of the Invention (Technical Field)

The invention relates to oscillator circuits and more particularly to oscillator circuits which operate with high loss resonators such as resonator sensors immersed in a liquid medium.

2. Background Art

This invention is an improvement over existing technology because of its simplicity, versatility, and functionality over existing devices. The circuit of the present invention can be used with a wider variety of sensor resonators (resistance and operating frequency) than is possible with current designs while not giving up the ability to measure the loss of the resonator in a simple manner. Additionally, the circuit can easily be adapted to a wide variety of applications.

Standard oscillator designs, like the Pierce or Colpitts type, are good for frequency source oscillator designs which provide low phase noise and high over-all frequency stability. These designs do not work well for sensor applications because of their inherent phase and gain sensitivity to resonator loss, $R_m$.

This design is technically different from existing oscillator designs designed for similar applications for the following reasons:

1. This design provides frequency and loss information in a grounded resonator configuration with a minimum of amount of complexity. No previous designs will allow frequency and loss measurements in a grounded resonator configuration with a simple design as presented, this is due to the fact that this oscillator exploits the loss of the resonator and uses the resonator impedance as in a divided form via the transistor feedback function. With the resonator impedance effectively decreased by feedback the oscillator can easily be controlled by high loss resonators.

2. This oscillator configuration combines many desirable features into one design:
   a. AGC controllable, for measuring $R_m$;
   b. wide bandwidth capable, high frequency resonators (>100 MHz) are operable in this design;
   c. simple design, low parts count, no unusual or expensive components required;
   d. grounded resonator configuration, test fixturing is simple and practical for many sensor application;
   e. oscillator operates at series resonance of resonator, this allows the widest dynamic range of resistance at lowest susceptibility to fixture capacitance problems.

U.S. Pat. No. 4,661,785 to Benjaminson discloses a balanced feedback oscillator that uses effective Q multiplication which yields lower phase noise oscillator for frequency source. This circuit cannot be used for high loss sensor resonator applications because the oscillator does not independently control phase and gain. Additionally, Benjaminson has a Miller effect which severely limits the frequency range possible for high accuracy operation. Although this design can operate a high loss resonator, it cannot actively or accurately control the frequency of oscillation to a predetermined resonator condition $f_s$ or impedance phase, over a wide range of resonator loss.

U.S. Pat. No. 3,986,145 to Hongu et al., and U.S. Pat. No. 5,025,231 to Schwartzbach disclose Colpitts type oscillators that do not utilize a series resonant frequency ($f_s$) design nor are the phase and gain functions independent for use as high-accuracy wide-dynamic range sensor oscillators.

U.S. Pat. No. 4,914,406 to Ohkubo is not a $f_s$ operating circuit and does not provide resonator loss information.

U.S. Pat. No. 5,113,153 to Soyer describes a Pierce oscillator design. This design along with Colpitts type designs are not adequate for high loss resonators because the oscillator frequency of operation is relatively sensitive to the resonator loss. These circuits are not useable in sensor-resonator applications because phase conditions and gain are dependent on each other.

SUMMARY OF THE INVENTION (DISCLOSURE OF THE INVENTION)

In accordance with the present invention there is provided an oscillator circuit for use with high loss resonators. The apparatus of the invention is preferably for use with resonators and comprises a high precision oscillator circuit for a resonator comprising an apparatus for controlling a frequency of oscillation to maintain a resonator impedance phase to a predetermined phase; and an automatic level control apparatus for determining resonator loss.

The preferred oscillator circuit comprises a differential amplifier. The preferred apparatus for controlling a frequency comprises a negative feedback structure. The preferred negative feedback structure comprises a low Q tank circuit in conjunction with a resistive feedback element. The negative feedback structure can also comprise a resistive element between the resonator and a tank circuit.

The negative feedback structure can also comprise structure for controlling a current gain of a resonator side of the differential amplifier. The preferred structure for controlling a current gain comprises a preselected feedback resistive element and a tank circuit resistive element.

The preferred oscillator circuit further comprises structure for operating the oscillator circuit over a wide dynamic range of resonator loss. The preferred structure for operating the oscillator circuit over a wide dynamic range of resonator loss comprises an apparatus for maintaining a phase over a range of resonator loss.

The preferred oscillator further comprises an apparatus for controlling gain of oscillation. The preferred apparatus for maintaining a phase over a range of resonator loss comprises structure for separating the phase from the apparatus for controlling gain.

The preferred apparatus for controlling gain comprises a voltage controlled current source for biasing the differential amplifier. The preferred wide dynamic range comprises a range from approximately ten (10) ohms to four thousand (4,000) ohms.

The preferred oscillator further comprises structure for attaching one side of the resonator to ground. The preferred oscillator circuit further comprises non-inverting signals. The preferred predetermined phase of the oscillator circuit is approximately 0°.

The preferred automatic level control for determining a resonator loss comprises structure for outputting a voltage proportional to resonator loss.

A primary object of the present invention is to provide a user with a specific oscillator for in situ sensor applications.

Another object of the present invention is to provide a circuit for use with high loss resonators.

A primary advantage of the present invention is its accuracy, simplicity and versatility.

Another advantage is that the Lever oscillator circuit keeps phase and gain independent from each other.

Yet another advantage of the present invention is that it can be used for in situ sensor applications.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS (BEST MODES FOR CARRYING OUT THE INVENTION)

Figure 1:
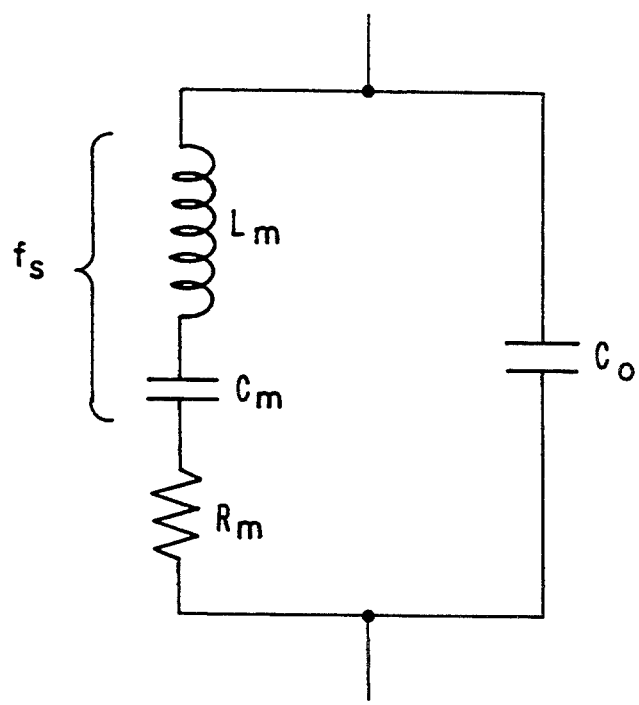
FIG. 1 is a schematic of a quartz resonator model.

There are a few oscillator configurations which operate resonators near the intrinsic emmiter impedance (h) and have one side of the resonator grounded. None of these configurations meet the design goals of operating at $f_s$ of the resonator and outputting a voltage proportional to the resonator loss or motional resistance of the resonator ($R_m$), by way of an automatic level control (ALC) circuit. For in situ resonator sensors the $R_m$ of the resonator will have a wide dynamic range. This dynamic range depends upon the resonator and liquid properties but could be tens of ohms in air to several thousand ohms in a viscous liquid. The resonator loss is a function of the viscosity-density product. Since quartz resonator frequency shifts due to a given environment are determined by calculating the change in $f_s$ of the resonator, a design is disclosed that operates as close to $f_s$ as possible such that the oscillator frequency mirrors the sensor-related frequency changes. In general if the impedance of shunt capacitor $C_o$, as shown in a quartz resonator model in FIG. 1, is relatively large compared to $R_m$, then $f_s$ is close to the frequency at which the resonator impedance phase is zero. The $R_m$ output voltage can also be used to determine the frequency error of the oscillator itself relative to true $f_s$ if the shunt capacitance across the resonator is relatively constant throughout the measuring medium.

Figure 2:
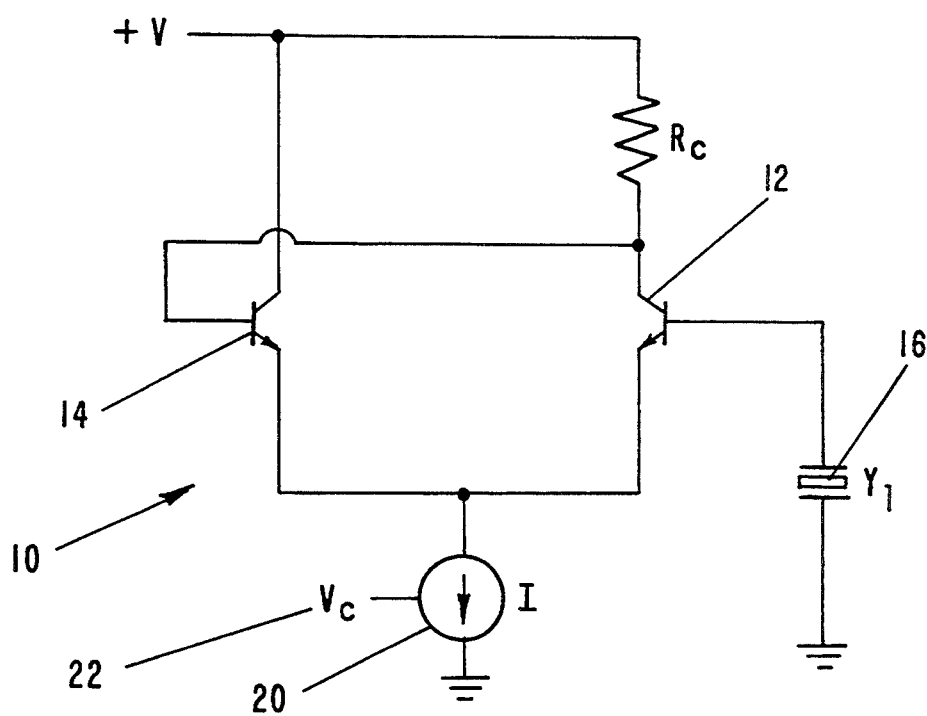
FIG. 2 is a schematic of a non-inverting amplifier as an oscillator.
Figure 3:
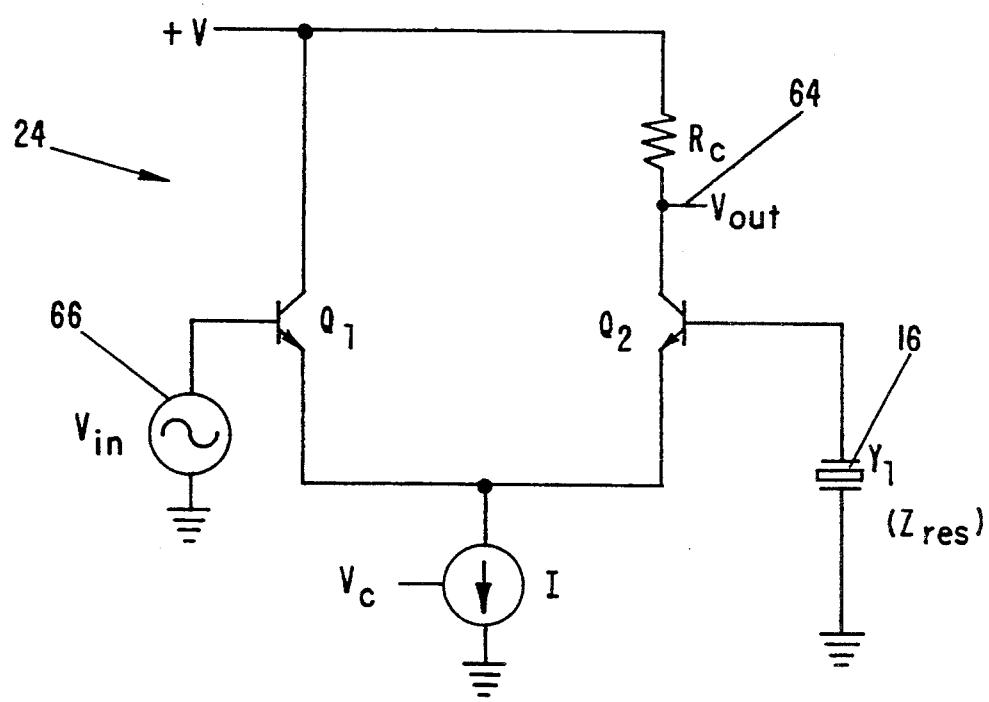
FIG. 3 is a schematic of an open-loop circuit for oscillator calculations.

FIG. 2 is schematic of an alternative embodiment of the Lever oscillator. In this oscillator circuit 10, collector of transistor 12 is directly connected to base of transistor 14 and resonator 16 is connected from base of transistor 12 to ground. Resonator 16 will control (poorly) the gain and phase of the potential oscillation. Current source 20 is controlled by $V_c$ 22 and will be used in an ALC circuit to servo a given oscillation amplitude and thus will reflect the resonator loss. Transistor h is the reciprocal of transconductance $g_m$ and is equal to $(26 \text{ mV})/I_e$ where $I_e$ is the individual transistor bias current. To determine the loop gain equations one could open the loop at the base of transistor 14 and determine the loop gain equation for the amplifier of FIG. 3. If the output impedance of the circuit is low relative to the input impedance the gain equation will be fairly representative of the actual oscillator. Equation (1) is the open loop gain equation for circuit 24 in FIG. 3. Circuit 24, when $V_{out}$ 64 is connected to $V_{in}$ 66, will oscillate when the voltage gain ($A_v$) is greater than or equal to one.

$$A_v \approx \frac{R_c}{2h + \frac{Z_{res}}{\beta}} \qquad (1)$$

Figure 4:
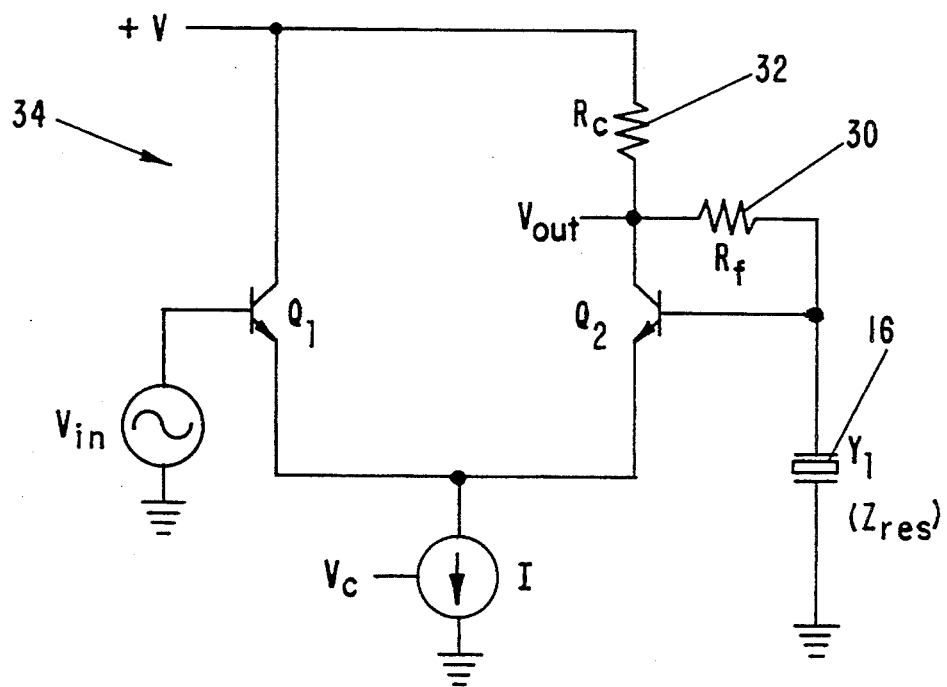
FIG. 4 is a schematic of the Lever oscillator open loop circuit.
Figure 5:
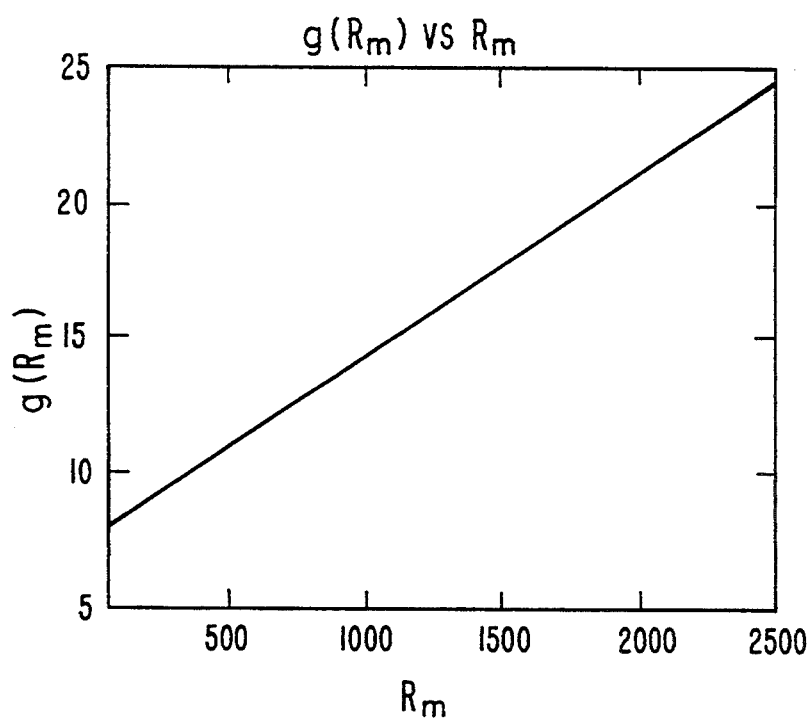
FIG. 5 is a graph of variable "lever effect", $g(R_m)$ vs. $R_m$.

If transistor 14 and transistor 12 are biased at current levels of approximately (0.1<I<10 mA), resonator 16 will weakly control oscillator 24 because the resonator impedance is divided by the transistor β. Since the loop gain is more dependent on transistor h than the resonator impedance the oscillator sensitivity to resonator resistance is poor and the loop phase of circuit 24 will not be very sensitive to the resonator 16 impedance. This circuit 24 would work well for the application described if the resonator 16 impedance was effectively divided by a smaller number (less than β) and was independent of transistor β. For example, it would be desirable to have the resonator impedance divided by a large number when resonator 16 is a high impedance and divided by a smaller number when resonator 16 is a low impedance. This variable divider would help to compress the dynamic range of the oscillator transconductance over a wide dynamic range of resonator loss while still allowing enough sensitivity to determine the resonator loss via an automatic level control (ALC) circuit. This function can be obtained by modifying oscillator 24, of FIG. 3 by placing a feedback resistor (not shown) from the collector of transistor 12 to the base of transistor 12. The Lever oscillator design (open loop) can be seen in FIG. 4. This schematic shows feedback resistor 30 $R_f$, that is used to make the oscillator sensitivity to resonator impedance a function of the resonator impedance itself. This function can be made β independent and will allow the resonator impedance to be effectively divided (leveraged) as a function of the magnitude of the resonator impedance. The Lever oscillator open loop gain, $A_v$ if $R_c$ 32 < $R_f$ 30:

$$A_v \approx \frac{R_c}{2h + \frac{Z_{res} \| [R_f + R_c]}{\beta} + \frac{R_c Z_{res}}{R_c + R_f + Z_{res}}} \qquad (2)$$

for oscillation $A_v$ must be greater than or equal to one where $Z_{res}$ is the magnitude of impedance of the resonator. If all the variables in equation (2) are real, then $Z_{res}$ must also be real (have a zero impedance phase). If $Z_{res}$ is real then the frequency of operation is close to $f_s$ of resonator 16 and the resonator impedance can be approximated by $R_m$. Equation (2) can be simplified to:

$$A_v \approx \frac{R_c}{2h + \frac{R_c R_m}{R_c + R_f + R_m}} \geq 1 \qquad (3)$$

where β is considered large enough to make the center term in the denominator of the loop gain equation (2) very small in comparison to the other two terms. The term $$\frac{R_c R_m}{R_c + R_f + R_m} \qquad (4)$$

is the "Lever" term, since it will determine how the resonator impedance is effectively divided (leveraged) by the feedback circuit elements, $R_c$ 32 and $R_f$ 30. $R_m$ is effectively divided by the function $$\frac{R_c + R_f + R_m}{R_c} \equiv g(R_m) \qquad (5)$$

which is small when the resonator impedance is small and large when the resonator impedance is large. The Lever term (4) is transistor β-independent and can be made to dominate the given gain equation (2) over a wide range of β. This variable leverage function allows the oscillator to operate over a wider dynamic range of resonator resistance while maintaining sensitivity at lower resonator resistances than if the divider effect was constant or dependent on β. FIG. 5 shows a graph of equation (5) vs $R_m$. This graph represents the variable divider effect the circuit has on $R_m$ with $R_c$ 32 equal to 150 ohms and $R_f$ 30 equal to 1000 ohms. Because circuit 34 of FIG. 4 is operating close to $f_s$ of resonator 16, $Z_{res}$ is approximately $R_m$ if $C_o$ is relatively small.

With the chosen values of $R_c$ 32 and $R_f$ 30, resonator impedance $R_m$ is effectively divided by 7 for small values of $R_m$ and by approximately 24 for large values of $R_m$. By selecting the values of $R_f$ 30 and $R_c$ 32 such that $R_f/R_c << \beta$, the oscillator will be relatively independent of β. The choice of $R_f$ 30 and $R_c$ 32 in combination with current source function 22 ($V_c$) allow setting the oscillator sensitivity to a desired range of $R_m$.

Figure 6:
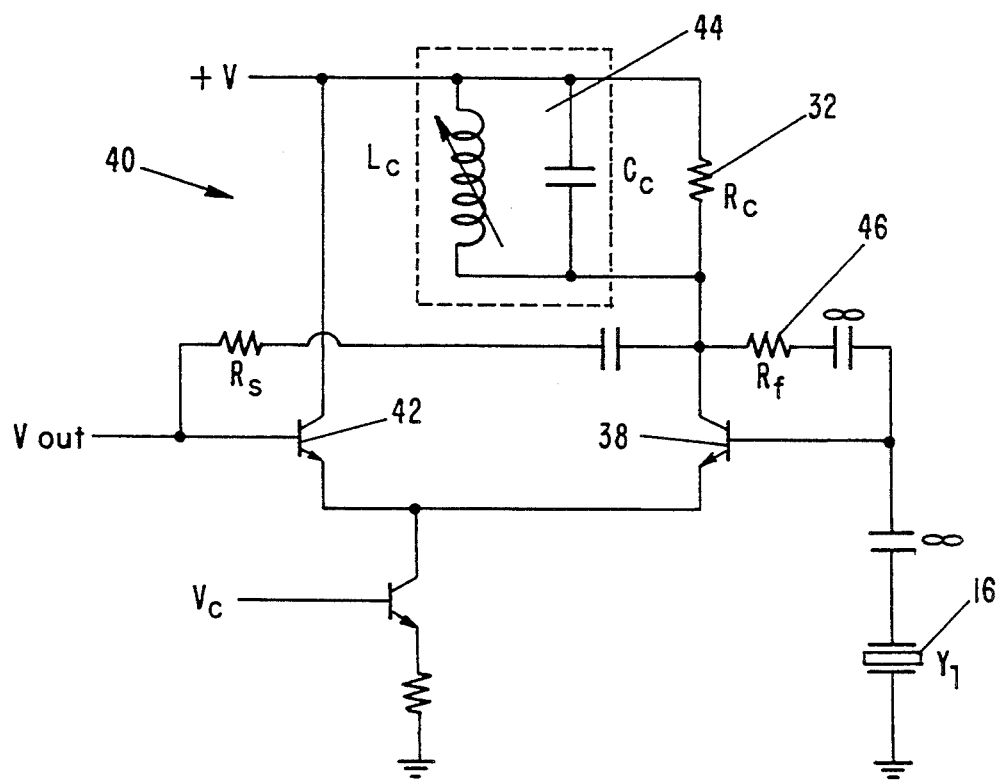
FIG. 6 is a schematic of the Lever oscillator schematic.

The oscillator theory presented to this point has virtually ignored transistor capacitances and the practical matters of the design. FIG. 6 is a schematic of a practical form of the Lever oscillator. In the discussion above it was stated that if all the circuit components shown (FIG. 4) were real then at the oscillation frequency resonator 16 would also be real. But in actuality, at frequencies greater than d.c., circuit capacitance will influence circuit performance. Capacitance from collector to ground of transistor 38 combined with base to ground capacitance of transistor 42 must be addressed. This capacitance, lumped together because of the circuit 40 configuration, significantly degrades circuit performance: (1) this capacitance pulls the oscillator low in frequency (even for a small amount of capacitance) and (2) if the resonator becomes highly lossy, circuit 40 has a tendency to jump to a parasitic (capacitor controlled) frequency. These two problems were minimized by placing a parallel L-C ($L_c$ and $C_c$) tank circuit 44 across $R_c$ 32. This tank 44 is designed to be low Q (1 to 3) and is used to make the collector to ground impedance at transistor 38 to be real (approximately $R_c$ 32) at the desired frequency and to help constrain the oscillation frequency to the resonator 16 and not to a parasitic frequency. Tank 44 is adjusted by using a resistor (not shown) with a low value, for example 100 ohms, in place of resonator 16. Tank circuit 44 is adjusted to make the oscillator frequency approximately equal to the desired resonator frequency. With $R_c$ real 32 at the resonator frequency, the discussion above is established.

The next matter to resolve for the theoretical basis of the invention is to determine the effect the feedback element has on the circuit if it is not real. Since $R_f$ 46 is a major component in the design, one must note the effect of capacitance across $R_f$ 46 due to the $C_{bc}$ of the transistor. By using equation (3), substituting $Z_{res}$ for $R_m$ and $Z_f$ for $R_f$ one can solve for $Z_{res}$ and determine the phase and magnitude of $Z_{res}$ as a function of $Z_f$, $R_c$ 32 and h.

$$Z_{res} \approx \frac{[R_c - 2h][R_c + Z_f]}{2h} \quad (6)$$

and if $R_c 32 < Z_f$ $$Z_{res} \approx \frac{[R_c - 2h][Z_f]}{2h} \quad (7)$$

where $R_c$ 32 and h are real. If these assumptions are good then it can be seen from equation (7) that the resonator impedance phase must be equal to the phase of $Z_f$. If operating close to zero impedance phase of the resonator 16 is desired, it is important to select $R_f$ 46 such that $R_f$ 46 is much less than the impedance of $C_{bc}$ for the chosen transistor. If a transistor having a $C_{bc}$ of approximately 3 pF is chosen and $R_f$ 46 of 1000 ohms is used, then the impedance, $Z_f$ for $R_f$ 46 in parallel with 3 pF at 6 MHz, will equal 994 ohms at −6.45°. For this case the resonator impedance phase at the oscillation frequency will also be approximately 6°. Although the equations derived herein are for small-signal low-excess loop-gain (one) conditions, the oscillator 40 essentially behaves as equation (6) predicts; this is true for two reasons: (1) the oscillator 40 will be used in an ALC circuit which is used to control the excess gain to a relatively low value so that $R_m$ can be determined and (2) the differential amplifier limiting characteristics provide a symmetrical limiting action that makes the circuit behave more linearly than a simple single-transistor oscillator circuit.

Figure 7A:
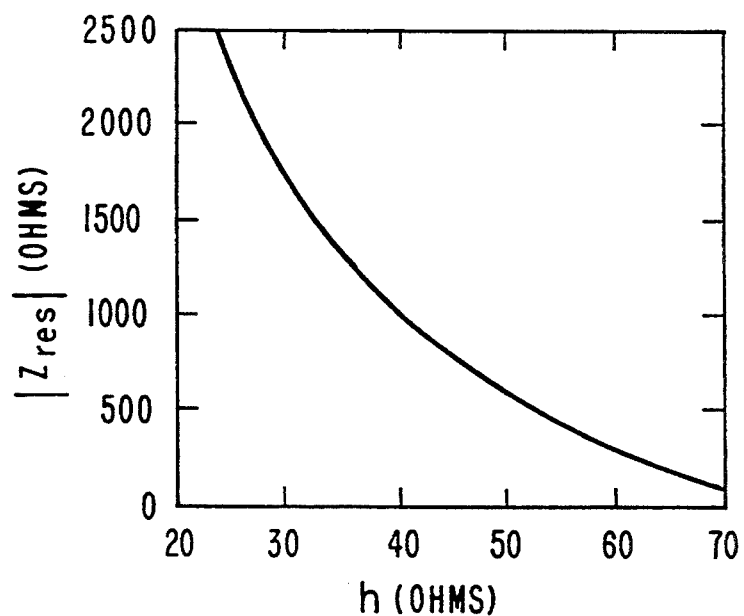
FIG. 7a is a graph of the calculated resonator impedance vs. transistor intrinsic emmiter impedance (h) for the Lever oscillator.
Figure 7B:
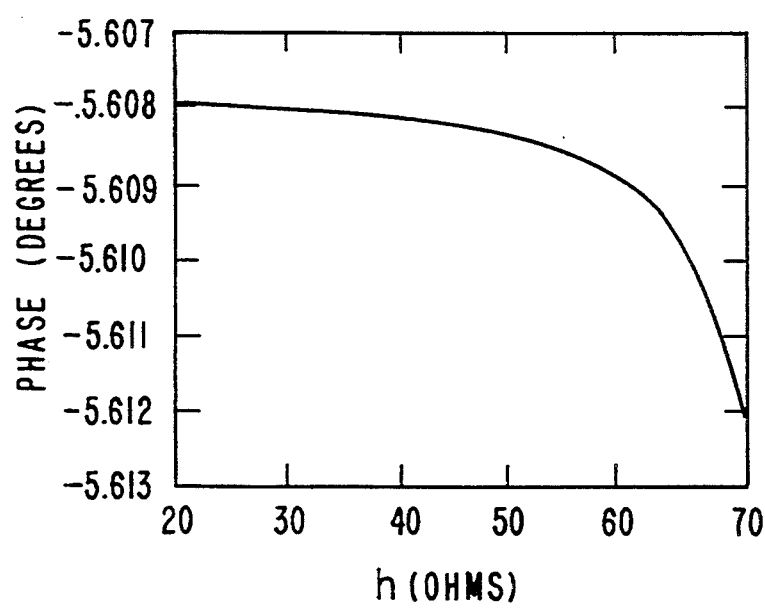
FIG. 7b is a graph of calculated resonator phase vs. h for the Lever oscillator.

FIG. 7 is a calculation of resonator impedance and phase versus transistor h using equation (6). This graph demonstrates the wide dynamic range of resonator impedance possible with the oscillator controlling the crystal impedance phase to approximately the phase of the feedback impedance $Z_f$.

To indirectly measure resonator resistance an ALC loop 48 was designed to control the oscillator gain (h) via the voltage controlled current source, transistor 50, (FIG. 8) of oscillator 52.

Figure 8:
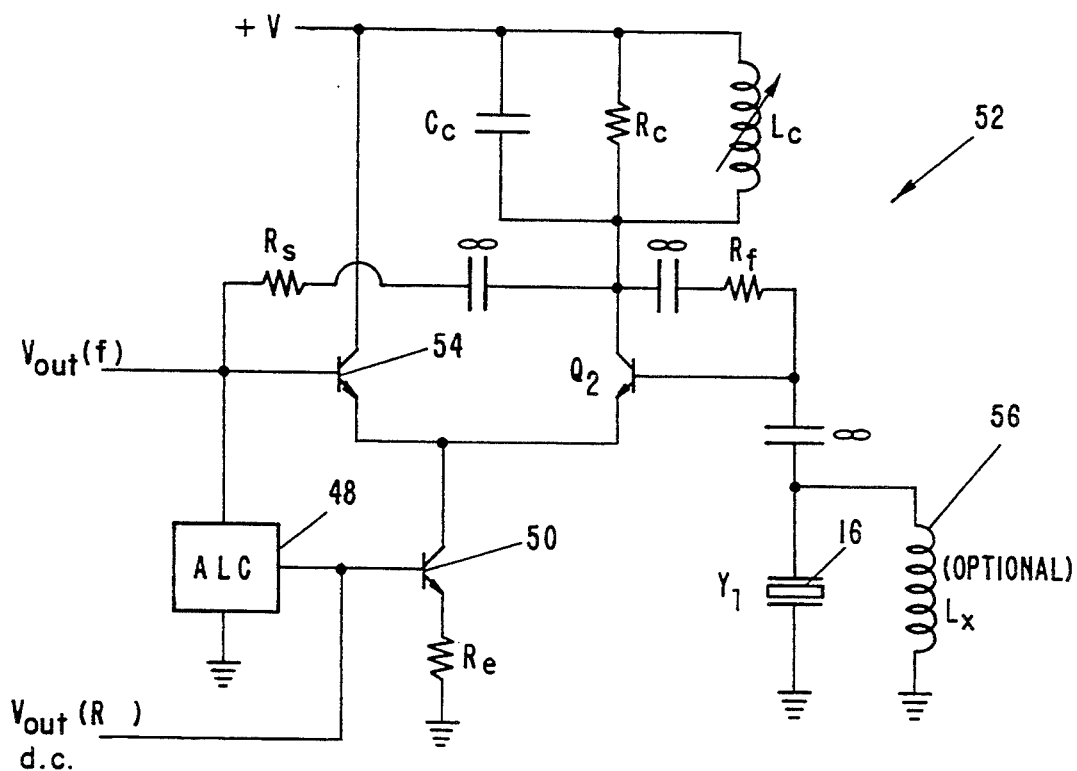
FIG. 8 is a schematic of an alternative embodiment of the Lever oscillator with automatic level control (ALC) circuit.

ALC 48 is designed to control the oscillation amplitude at the base of transistor 54 to approximately 200 mV peak-to-peak. FIG. 8 also shows inductor $L_x$ 56 which can be used to tune out static capacitance of the fixture and resonator 16. $L_x$ 56 can dramatically increase the upper resistance limit before the oscillator breaks into a parasitic oscillation.

Figure 9:
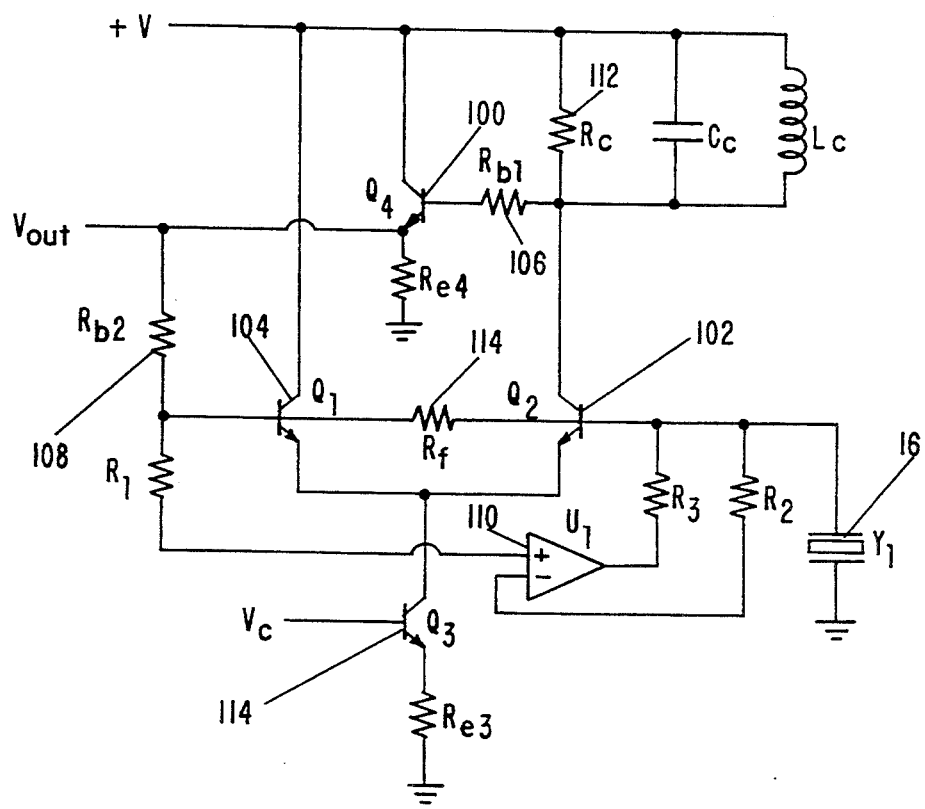
FIG. 9 is a schematic of the preferred embodiment of the Level oscillator.

FIG. 9 is a schematic of the preferred Level oscillator. The preferred embodiment has a low output impedance for driving a buffer amplifier. Transistor 100 provides this low output impedance and provides the a.c. connection of signals from the collector of transistor 102 and the base of transistor 104 (the positive feedback). Resistors 106 and 108 are low value resistors, for example 50 ohms, and are required for rejection of high frequency spurious oscillations and have no effect on the circuit operation. This embodiment has active biasing by transistor 100 and operational-amplifier 110 and requires fewer d.c. decoupling capacitors than other designs (FIG. 8). This circuit is suited for integration which is important when size is a factor. Another benefit derived from this embodiment is that it works over a wide variation of design parameters of $R_c$ 112 and $R_f$ 114 due to the biasing and a.c. circuit configuration provided by the addition of transistor 100. For example, if $R_f$ 114 is placed between the bases of the differential amplifier (transistors 102 and 104) and is isolated from the collector of transistor 102, a low value of $R_f$ 114 can be utilized.

Operational-amplifier 110 is used to force the bases of transistors 102 and 104 to be at the same d.c. bias voltage, which is independent of the value of $R_f$ 114. Operational-amplifier 110 is not required if a small offset in the differential amplifier can be tolerated. This offset depends upon the amplitude of the bias currents and the value of $R_f$ 114.

There are numerous applications for an oscillator circuit capable of operating a quartz resonator in contact with fluid. The resonant frequency can be used to indicate mass accumulation on the crystal face. The applications of this microbalance capability include:

(1) Deposition monitoring—For electrodeposition processes (e.g., electroplating) and electro-less deposition processes on non-conductive substrates (e.g., in making printed circuit board).

(2) Chemical Sensing—By coating the crystal with a chemically sensitive layer, species in solution can be sensed. Applications include pollution monitoring, trace contaminant detection (e.g., heavy metals), and biochemical sensors for medical application (e.g., immunoassay). Additionally, quartz oscillator sensors coated with chemically selective enzymes can be used as environmental monitors.

The circuit's ability to provide information on crystal damping allows the device to be used to measure properties of the contacting liquid also. Liquid density and viscosity can be inferred from measurements on resonant frequency and damping.

Industrial Applicability:

The invention is further illustrated by the following non-limiting examples.

EXAMPLE I

To evaluate the Lever oscillator for one set of circuit parameters, a 6 MHz test resonator was made using a standard low resistance device in series with added resistance. FIG. 8 shows the test resonator used to evaluate the Lever oscillator.

Figure 10:
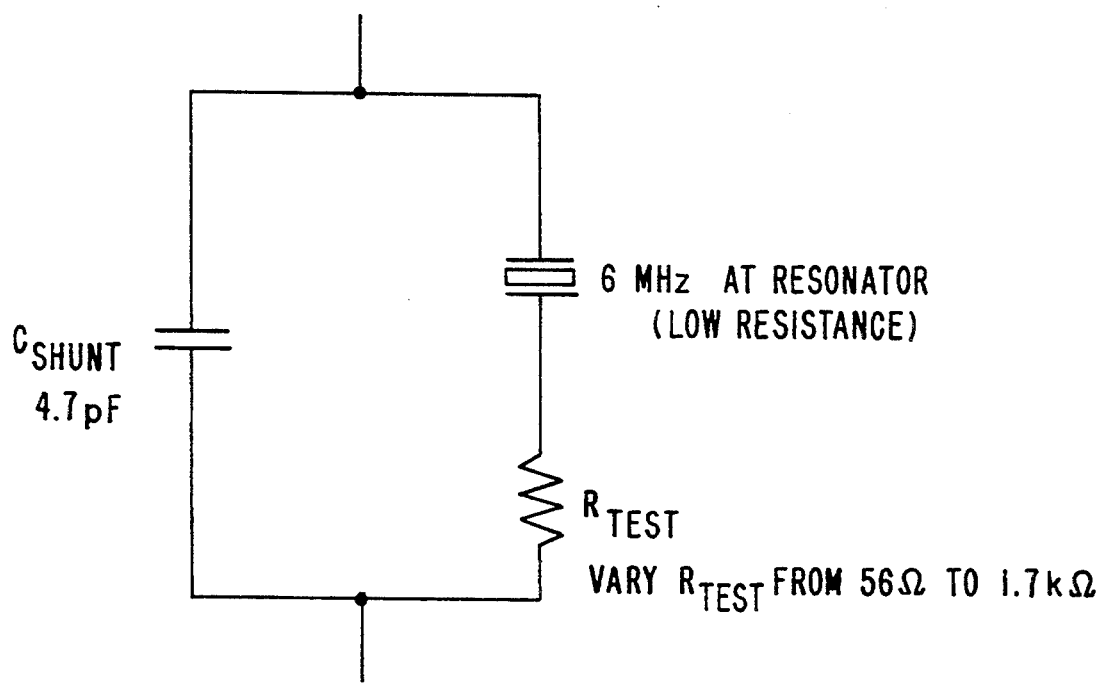
FIG. 10 is schematic of a test resonator with variable resistance.
Figure 11:
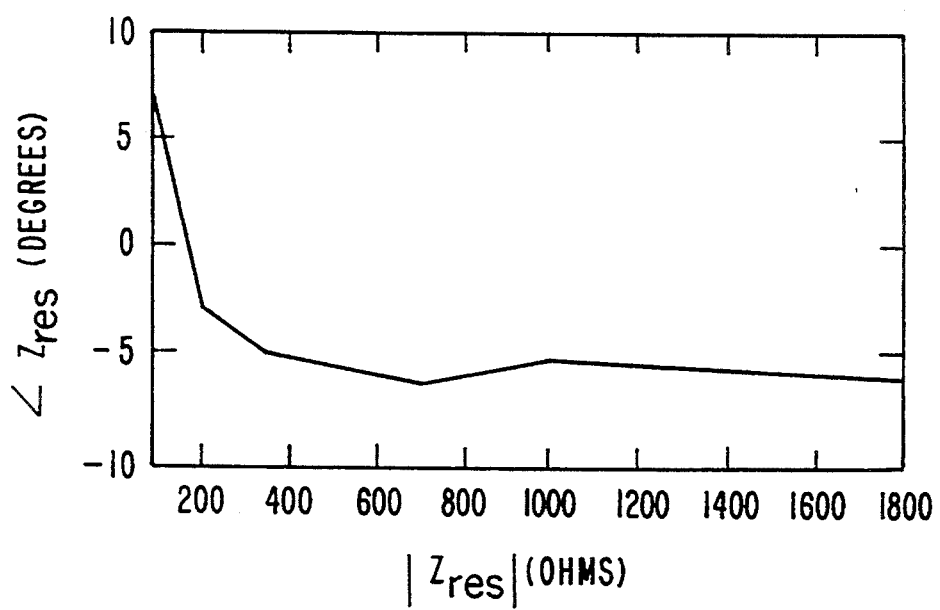
FIG. 11 is a graph of measured resonator impedance phase vs. magnitude.

$C_{shunt}$ 58 was included in the test resonator 60 to more accurately simulate the $C_o$ of a standard resonator. This resonator 60 was used to determine the actual resonator impedance phase at oscillation for a wide range of resistance, $R_{test}$ 62. $R_{test}$ 62 was varied from 56 to 1700 ohms and the resonator impedance was measured on an impedance analyzer at the frequency of operation of the Lever oscillator for each tested resistance. Also the d.c. voltage of the ALC was recorded for all values of $R_{test}$. Data relating resonator impedance, phase, and d.c. output voltage as a function of $R_{test}$ are presented in FIGS. 10 and 11 respectively.

Figure 12:
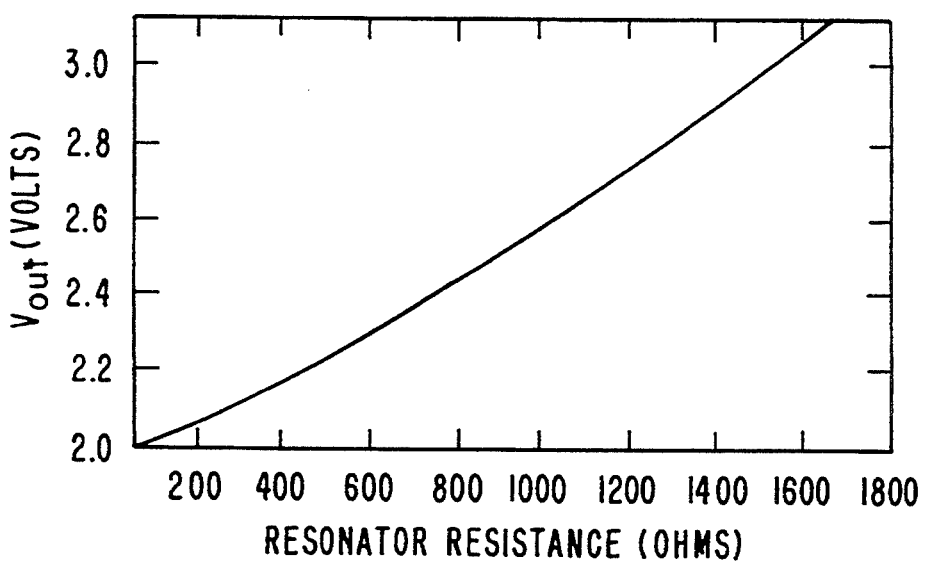
FIG. 12 is a graph of ALC voltage out vs. resonator resistance.
Figure 13:
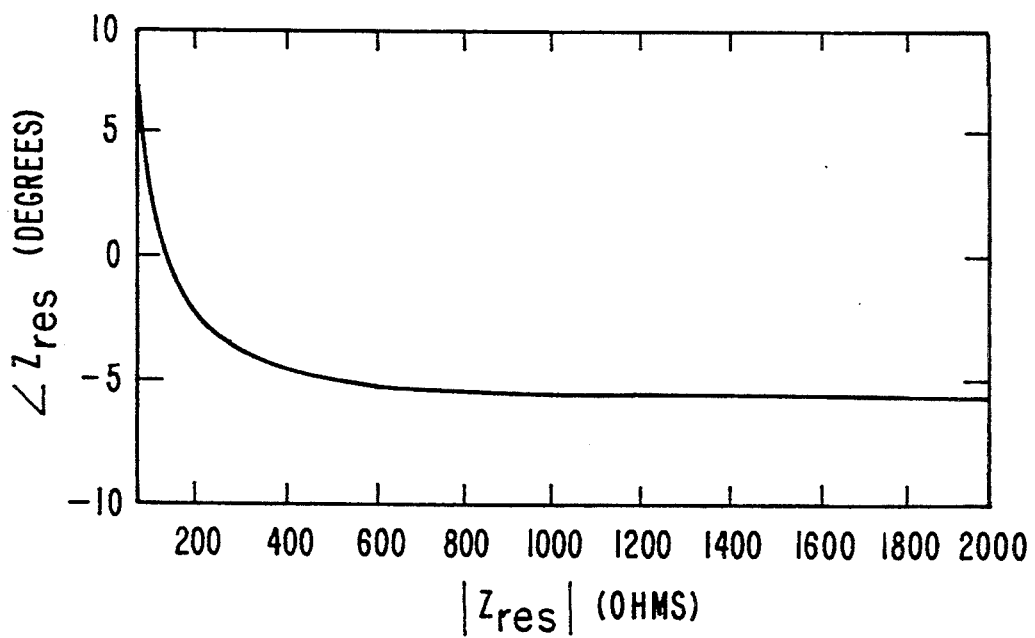
FIG. 13 is a graph of the calculation of resonator impedance phase vs. magnitude for h slightly capacitive.

These data demonstrate that the oscillator does indeed servo the resonator impedance to approximately the phase of $Z_f$ in this case approximately 6°, when resonator 16 is above 200 ohms. At resonator impedances below 200 ohms resonator impedance phase increases. This phase shift at low resonator impedances is explained by the fact that oscillator is less controlled by resonator 16 when the resonator impedance is low than when large and is therefore more sensitive to circuit parameters not used in the approximations presented here. To illustrate this, a more exact model of the oscillator was used which assumed the transistor h to be very slightly capacitive. When this capacitance is included in the calculations, the resonator impedance phase increases with decreasing resonator impedance just as seen in the data in FIG. 11 and 12. FIG. 13 shows the calculated magnitude of $Z_{res}$ versus the phase of $Z_{res}$ with transistor h slightly capacitive.

Figure 14:
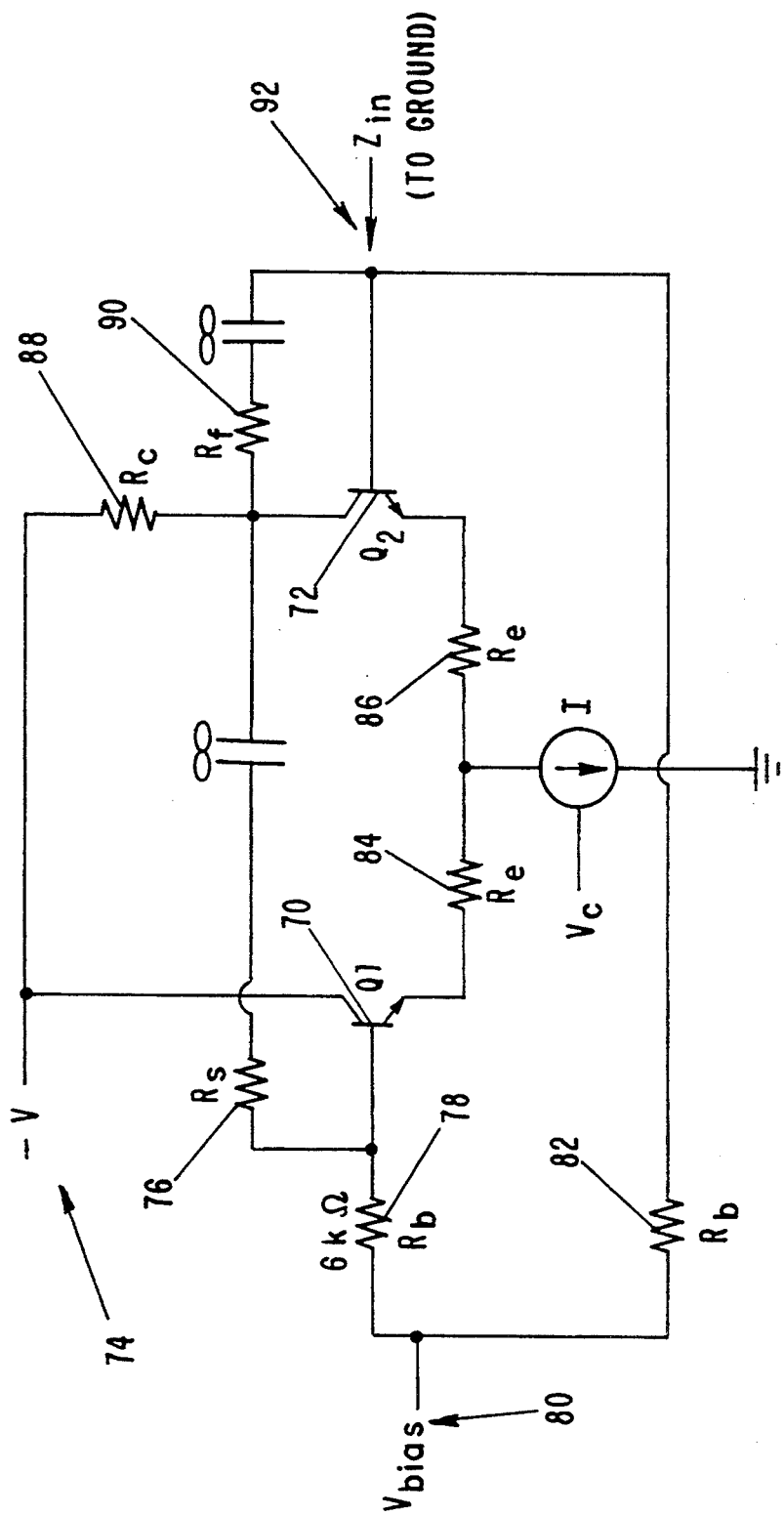
FIG. 14 is a schematic of the preferred Lever oscillator circuit used in negative resistance model calculations.

To demonstrate the $\beta$ insensitivity of the Lever oscillator, a negative resistance model can be used to calculate the input impedance ($Z_{in}$) 92; the calculations are shown in FIG. 14 as a function of h for transistor $\beta$'s of 150 and 50 where $R_e$ is the internal transistor resistance. The following components values are used in the model:

+v 74 = 5 v
$R_s$ 76 = 100Ω
$R_b$ 78 = 6 kΩ
$V_{bias}$ 80 = 4 v
$R_b$ 82 = 6 kΩ
$R_e$ 84 = 3Ω
$R_e$ 86 = 3Ω
$R_c$ 88 = 140Ω
$R_f$ 90 = 1 kΩ

Figure 15:
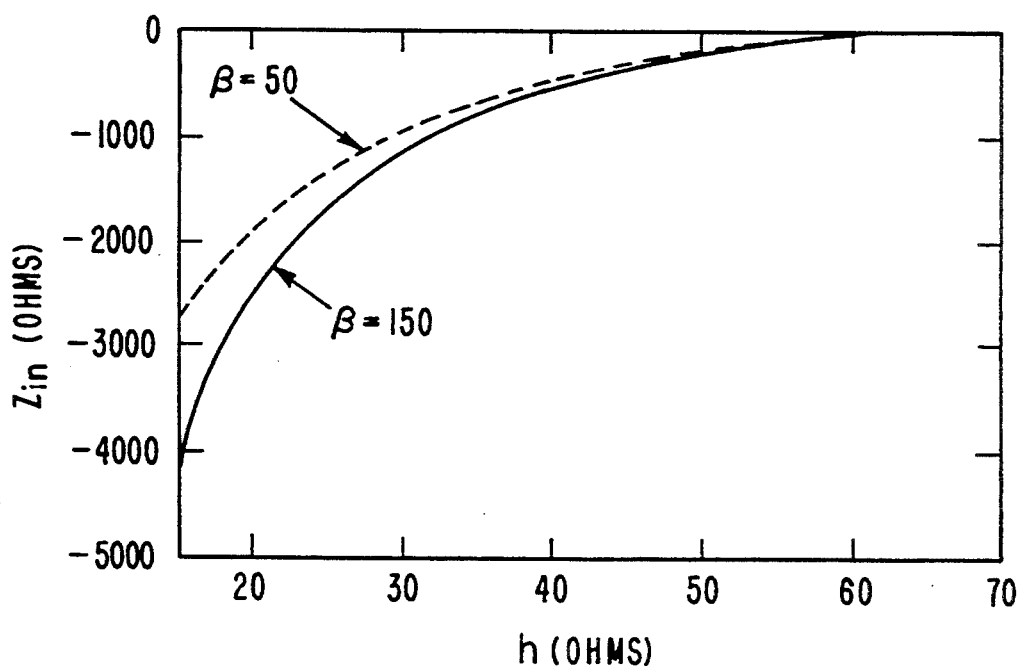
FIG. 15 is a graph of calculations of $\beta$ sensitivity vs. h.

FIG. 15 is a graph of the negative resistance function of the Lever oscillator for $\beta$ equal to 50 and 150. The oscillator $\beta$ sensitivity is greatest at high resonator resistances where the negative feedback due to $R_f$ 90 and $R_c$ 88 is least effective. With the feedback used in this example, the oscillator is relatively insensitive to transistor $\beta$ for h between 20 and 65 ohms.

Figure 16:
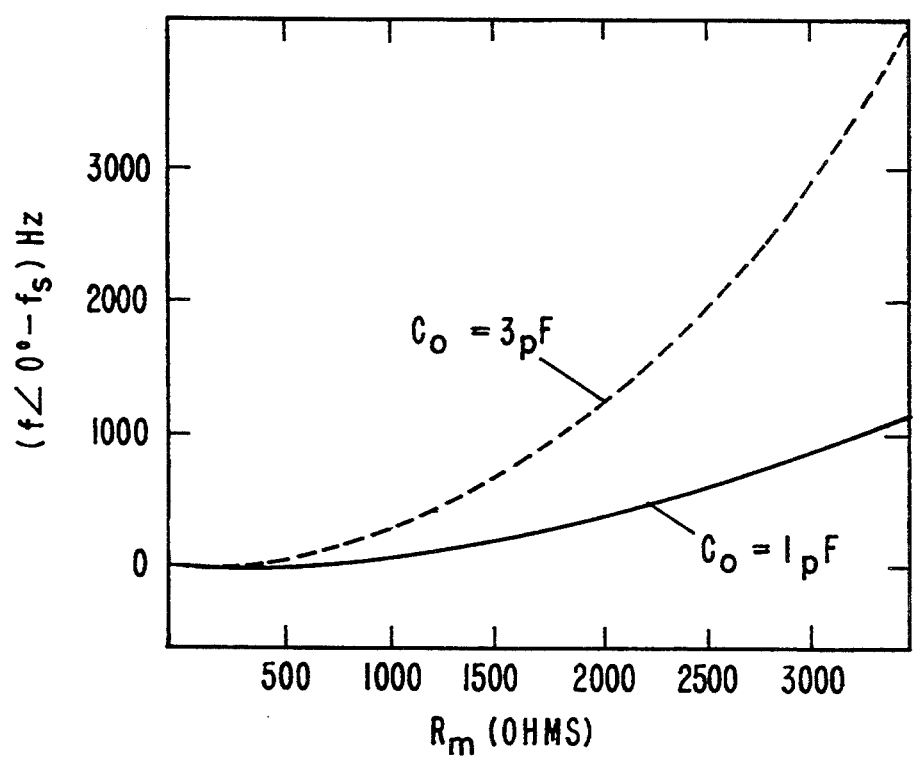
FIG. 16 is a graph of calculated difference between the frequency of zero impedance phase of the resonator and $f_s$ of the resonator.
Figure 17:
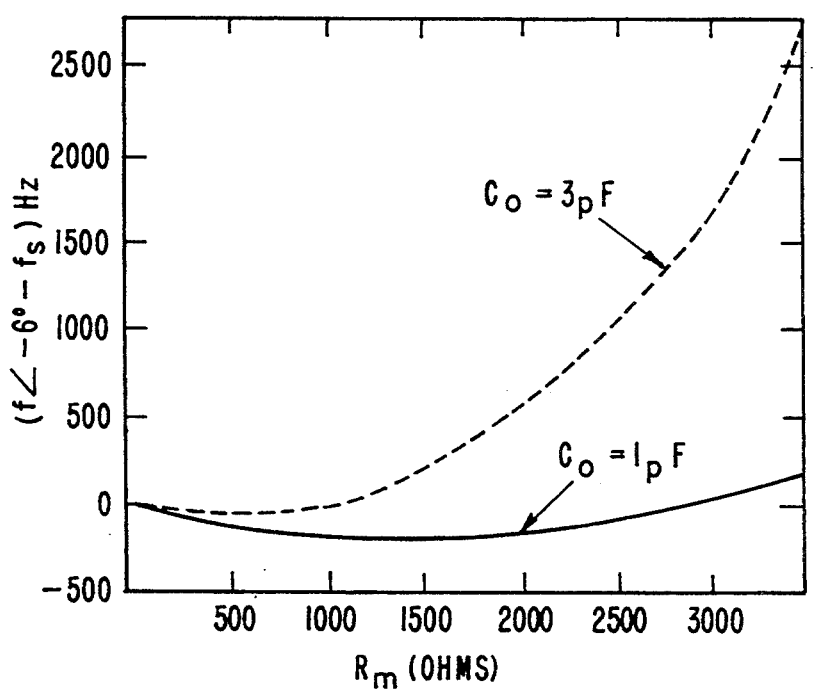
FIG. 17 is a graph of the calculated difference between the frequency at $-6°$ impedance phase and $f_s$ of the resonator.

Now that it has been established that the Lever oscillator function acts like an impedance phase servo it is necessary to determine how this phase frequency relates to the true $f_s$ of resonator 16. If $C_O$ is zero then $f_s$ is equal to the zero impedance phase frequency. But since $C_o$ is never zero then the oscillation frequency of the Lever oscillator will be offset from true $f_s$ of resonator 16 by some amount depending on $R_m$, $C_o$, and the phase of the resonator impedance which the oscillator is servoing. FIG. 16 is a graph showing the calculated difference between the frequency of zero impedance phase and $f_s$ of resonator 16. This is done for two static capacitances of resonator 16, 1 pF and 3 pF. FIG. 16 shows that, for $C_o$ equal to 1 pF, the frequency error with $C_m$ equal to 25 pF and $L_m$ equal to 31 mH is relatively small but increases with resonator resistance $R_m$. With increasing $C_o$ the frequency error increases dramatically with $R_m$. FIG. 17 is a graph of the same function but in this case a difference frequency for −6° of impedance phase and $f_s$ is calculated and the resulting curve shows a negative error for small $R_m$, sweeping positive as the resistance increases. This is to be expected since at $f_s$ the resonator is essentially a capacitance ($C_o$) in parallel with resistance ($R_m$). Therefore, the resonator impedance phase at $f_s$ is a negative quantity varying with $R_m$ and/or $C_o$. To make a "true"$f_s$ oscillator one would have to vary the phase that the oscillator servos as a function of $R_m$ given a fixed $C_o$. Due to the fact that the Lever oscillator has a $R_m$-sensitive output voltage, one can use this output to correct for the frequency error calculated in FIGS. 16 and 17 if such accuracy is required. This correction could be implemented using digital analog techniques.

EXAMPLE II

Figure 18:
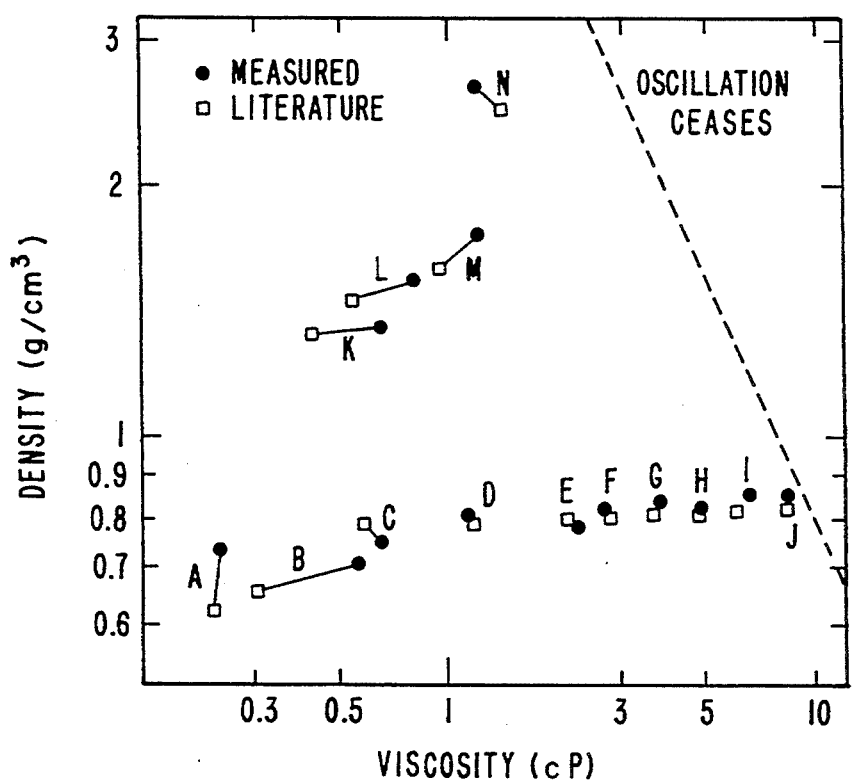
FIG. 18 is a "scatter diagram" of measurements made with the preferred embodiment for different liquids compared to literature values in Example II.

The Level oscillator of FIG. 8 was constructed and utilized with a smooth faced and a textured faced resonator to determine liquid density and viscosity of liquids with known characteristics. The output data used in known resonator calculations to determine viscosity and density of liquids by measuring $f_s$ and $R_m$ from the Level oscillator were compared to literature values of liquid density and viscosity. FIG. 18 shows a comparison of the known (literature values) and extracted values of liquid density and viscosity for glycerol/water mixtures and organic solvents. The outputs as measured by the level oscillator are represented by circles with literature values shown as squares. The liquid corresponding to each set of points is indicated in Table I.

TABLE 1

| A | n-pentane | H | n-hexanol |
|---|---|---|---|
| B | n-hexane | I | n-heptanol |
| C | methanol | J | n-octanol |
| D | ethanol | K | dichloromethane |
| E | n-propanol | L | trichloroethylene |
| F | n-butanol | M | carbon tetrachloride |
| G | n-pentanol | N | dibromomethane |

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above, and of the corresponding application(s), are hereby incorporated by reference.

What is claimed is:

1. A high-precision oscillator circuit for a quarts resonator, the oscillator circuit comprising:
   differential amplifier means comprising negative feedback means for controlling a frequency of oscillation to maintain a resonator impedance phase to a predetermined phase; and
   a variable transconductance means comprising a current source for an automatic level controls, wherein said automatic level control comprises a means for outputting a voltage proportional to resonator loss, wherein said automatic level control regulates an amplitude of oscillation, thereby controlling a level of excess transconductance to relatively low levels for determining said resonator loss, whereby said oscillator circuit operates over a wide dynamic range of said resonator loss.

2. The invention of claim 1 wherein said negative feedback means comprises a tank circuit means in conjunction with a resistive feedback means.

3. The invention of claim 1 wherein said negative feedback means comprises resistive elements.

4. The invention of claim 3 wherein said resistive elements comprise means for concurrently physically selecting $R_c$ and $R_f$ for sensitivity, dynamic range and frequency of operation.

5. The invention of claim 1 wherein said wide dynamic range of resonator loss comprises means for maintaining a phase over a range of resonator loss.

6. The invention of claim 5 further comprising means for controlling a gain of oscillation.

7. The invention of claim 6 wherein said means for maintaining a phase over a range of resonator loss comprises means for separating said phase from said means for controlling a gain of oscillation.

8. The invention of claim 5 wherein said wide dynamic range comprises a range from approximately ten (10) ohms to approximately four thousand (4,000) ohms.

9. The invention of claim 1 further comprising means for attaching one side of the resonator to ground.

10. The invention of claim 1 wherein said oscillator circuit comprises a non-inverting signal means.

11. The invention of claim 1 wherein said predetermined phase is approximately 0°.

12. The invention of claim 1 wherein said differential amplifier means further comprises an output, an inverting input and a non-inverting input.

13. The invention of claim 12 wherein said negative feedback means comprises a first resistive element from said output to said inverting input and the resonator connected from said inverting input to ground and further comprises positive feedback.

14. The invention of claim 13 wherein said positive feedback comprises an output signal applied to said non-inverting input via a member selected from the set of a second resistive element and a buffer amplifier.

15. The invention of claim 14 wherein said second resistive element comprises a value less than 100 ohms.

* * * * *

UNITED STATES PATENT AND TRADEMARK OFFICE
CERTIFICATE OF CORRECTION

PATENT NO    : 5,416,448
DATED        : May 16, 1995
INVENTOR(S)  : Wessendorf

It is certified that error appears in the above-identified patent and that said Letters Patent is hereby corrected as shown below:

>Title page, item [75],
>The name of the inventor on the patent is changed to:
>
>KURT O. WESSENDORF Signed and Sealed this Sixth Day of April, 1999

Attest:

Q. TODD DICKINSON

*Attesting Officer*    *Acting Commissioner of Patents and Trademarks*